United States Patent [19]
Van Gysel et al.

[11] Patent Number: 6,069,280
[45] Date of Patent: May 30, 2000

[54] PROCESS FOR THE MANUFACTURE OF METHYLAMINES

[75] Inventors: August Van Gysel, Dilbeek; Jean Passelcq, Braine-l'Alleud, both of Belgium

[73] Assignee: UCB, S.A., Brussels, Belgium

[21] Appl. No.: 08/981,692

[22] PCT Filed: Jul. 5, 1996

[86] PCT No.: PCT/BE96/00072

§ 371 Date: Jan. 6, 1998

§ 102(e) Date: Jan. 6, 1998

[87] PCT Pub. No.: WO97/02891

PCT Pub. Date: Jan. 30, 1997

[30] Foreign Application Priority Data

Jul. 7, 1995 [GB] United Kingdom .................... 9513943

[51] Int. Cl.⁷ ................................................. C07C 209/00
[52] U.S. Cl. .............................. 564/479; 502/62; 502/63; 502/64; 502/85; 502/78
[58] Field of Search .................................. 502/63, 64, 62, 502/85, 78; 564/479

[56] References Cited

U.S. PATENT DOCUMENTS 5,137,854  8/1992  Segawa et al. ............................ 502/64
5,382,696  1/1995  Kiyoura et al. .......................... 564/479

*Primary Examiner*—Tom Dunn
*Attorney, Agent, or Firm*—Wenderoth, Lind & Ponack, L.L.P.

[57] ABSTRACT

Process for the preparation of a modified ammonium mordenite, characterized in that it comprises the steps of (1) drying an ammonium mordenite under conditions such that the mordenite is maintained in ammonium form and (2) treating the dried ammonium mordenite thus obtained with tetrachlorosilane in the gas phase at a temperature of between 300 and 600° C.

The modified ammonium mordenite obtained by this process is suitable for use as a catalyst in the production of methylamines by reaction of ammonia and methanol, allowing high selectivities in dimethylamine.

17 Claims, No Drawings

PROCESS FOR THE MANUFACTURE OF METHYLAMINES

This application is a 371 of PCT/BE96/00072 filed Jul. 5, 1996 which is based on U.K. 9513943.2, filed Jul. 7, 1995.

The present invention relates to a process for the preparation of a modified ammonium mordenite, and in particular to a catalyst comprising this modified ammonium mordenite prepared by said process, as well as to a process for the manufacture of methylamines by reaction of methanol with ammonia in the gas phase at elevated temperature, and optionally at elevated pressure, in which said catalyst is used.

In the catalytic synthesis of methylamines from ammonia and methanol, a vaporized mixture of methanol and ammonia is first prepared, which is next reacted in a reactor at temperatures of approximately 220 to approximately 500° C. at pressures between atmospheric pressure and approximately 50 bars, by passing over a catalyst bed.

The product of the reaction between ammonia and methanol consists of a mixture of three amines, monomethylamine (abbreviated to MMA), dimethylamine (abbreviated to DMA), trimethylamine (abbreviated to TMA), water, ammonia and unreacted methanol. In addition, dimethyl ether (abbreviated to DME) may be formed as by-product. Among these products, dimethylamine is the amine most sought after as far as industry is concerned; it is actually used, as raw material for the manufacture of many commercial products such as solvents, pharmaceutical products, vulcanization accelerators, surfactants, fungicides (for example tetramethylthiuram disulphide) and the like. The production of dimethylamine from ammonia and methanol necessarily involves a step of separation of the products obtained after the reaction. However, isolation of dimethylamine by distillation from the mixture of methylamines is considerably complicated by the fact that residual ammonia and the methylamines produced form azeotropic mixtures.

At the present time, methylamines are manufactured on an industrial scale from methanol and ammonia, using in most cases amorphous silica-alumina catalysts, because these catalysts have outstanding catalytic properties.

However, the mixture of methylamines obtained in the presence of these catalysts contains a major proportion of trimethylamine and, consequently, the production of the desired dimethylamine is insufficient.

This is why many investigations have been carried out in order to find catalysts which allow to obtain dimethylamine selectively while suppressing the production of trimethylamine as much as possible. The quantities of the various methylamines in the reaction product are determined by the thermodynamic equilibrium of the reaction; these quantities depend, among other parameters, on the reaction temperature and on the molar ratio of the reactants. For example, in the case of a reaction temperature of 300° C., an ammonia and methanol feed corresponding to an N/C atomic ratio of 2:1 and a methanol feed rate of 0.3 kg/h/kg of catalyst, the composition, in % by weight, of the mixture of methylamines at equilibrium is 20% MMA, 22.5% DMA and 57.5% TMA for an active but nonselective catalyst, when total conversion of methanol is achieved. This product composition corresponds to the thermodynamic equilibrium composition. Trimethylamine is thus produced predominantly under these conditions.

On the other hand, if the production of trimethylamine were suppressed, the composition in % by weight of the mixture of MMA and DMA at equilibrium would be 31.5% MMA and 68.5% DMA under the same conditions and when total conversion of methanol is achieved.

One can immediately see the interest in developping selective catalysts which prevent almost completely the production of trimethylamine.

A large number of catalysts have been proposed in order to reach this objective. The literature mentions, in particular, synthetic or natural zeolites like, for example, zeolites X, Y, ZK-5, ZSM-5, ZSM-12, FU-1, SK, erionite, ferrierite, faujasite, chabasite, clinoptilolite and more particularly mordenite. These zeolites have been used either as such or after having been subjected to various treatments in order to modify their characteristics, such as the number of acidic sites, the pore size or the silicon/aluminium ratio. The proposed treatments include, inter alia, the modification of the nature and of the proportion of the cations, treatment with acids, calcination with or without the presence of steam, or silylation by means of various silylating agents. The various proposed treatments may result in some improvement in the catalytic activity and/or in selectivity for the production of monomethylamine or dimethylamine.

However, when these zeolites are used as catalysts, the selectivity for the production of dimethylamine generally remains relatively low. Very often, the values obtained are very close to the values which can be obtained when thermodynamic equilibrium between the three methylamines is obtained.

For instance, in a paper relating to the selective synthesis of dimethylamine from methanol and ammonia in the presence of various zeolites (I. Mochida et al., J. Catal., 82, (1983), 313–321), the authors report that the best methanol conversions and selectivities for dimethylamine are obtained with mordenites (Zeolon from the company Norton Co. Ltd) in protonic form or in a form in which the cations are exchanged with sodium, magnesium or lanthanum-hydrogen cations. In this last form and for a reaction temperature of 400° C., a methanol conversion as high as 94.5% by mole and a selectivity for DMA of 51.5% by mole are obtained. The quantity of trimethylamine formed is, however, far from being negligible, since the selectivity for TMA reaches 11.9% by mole.

In U.S. Pat. Nos. 5,137,854 and 5,210,308, this disadvantage is overcome by using a proton mordenite which has undergone a specific treatment. This treatment consists in subjecting a sodium mordenite to a treatment with tetrachlorosilane in the gas phase, at elevated temperature (approximately 700° C. in the example) and, in converting the sodium mordenite thus treated to a proton mordenite by ion exchange. For this exchange, the sodium ions of the treated mordenite are exchanged with ammonium ions and the ammonium mordenite thus obtained is subjected to calcination for several hours at 450° C. According to these patents, this mordenite treatment does not appreciably modify its Si/Al atomic ratio, in other words, the mordenite does not undergo dealumination. This modified mordenite allows to obtain a methanol conversion of 98.9% by mole and a selectivity for dimethylamine of 61.2% by mole. The process described in these patents therefore provides a good methanol conversion and a good selectivity for dimethylamine. However, the production of trimethylamine remains high (see Example 4 below).

An attempt to solve this problem was also made in European Patent Application 593,086, which proposes a process for the preparation of methylamines allowing to produce monomethylamine and dimethylamine selectively and to reduce the production of trimethylamine to a few %. For this purpose, the synthesis of methylamines is performed in the presence of a specific catalyst. This catalyst is formed by first subjecting a proton mordenite to one or more silylation treatments with a silylating agent in liquid phase and then performing a heat treatment at a temperature of 300 to 600° C. in the presence of air or oxygen. The silylation treatment is performed by dispersing the mordenite in a solution of the silylating agent in a solvent. However, before the silylation treatment, the water content of the mordenite must be adjusted to a predetermined value. Thus, when the solvent used is water-soluble (for example an alcohol), the mordenite is calcined at a temperature of 350 to 600° C. until its water content is of 4% by weight or less. When the solvent used is not water-miscible (benzene and the like), the mordenite must contain from 3 to 40% by weight of water before being treated with the silylating agent; this water content is obtained either by controlled drying of the mordenite or by calcination and conditioning in a moist atmosphere.

This process allows to reach a very good selectivity for dimethylamine (approximately 64%). However, methanol conversion is only of approximately 90%, which means that, on an industrial scale, application of this process will require recycling of a significant quantity of unconverted methanol. Moreover, these results are obtained at the price of an elaborate and tricky technology. Indeed, several calcinations at high temperature in the presence of air are required for the preparation of the catalyst; furthermore, before the silylation treatment, the water content of the mordenite has to be controlled scrupulously, otherwise it is not possible to keep the production of trimethylamine at a low level (see, in particular, Examples 3, 6 and 8 of this patent application).

Therefore, despite the availability of many catalysts for the catalytic synthesis of methylamines from ammonia and methanol, there is still a need to find a catalyst which is, at the same time, (a) highly selective for the production of monomethylamine and of the desired dimethylamine (allowing, for example to achieve dimethylamine selectivities of 70% by mole or more), producing at the same time practically no trimethylamine or by-products, especially dimethyl ether;

(b) highly active, in order to bring the reaction to very high methanol conversions, preferably close to 100% by mole (to avoid recycling of methanol);

(c) capable of being prepared by a process that can be easily and economically carried out on an industrial scale.

We have now found, quite surprisingly, that it is possible to prepare a highly active and extremely selective catalyst from an ammonium mordenite, when this mordenite is subjected to a specific silylation treatment with tetrachlorosilane in the gas phase under specific conditions.

We have indeed found that by using this specific catalyst based on an ammonium mordenite in the synthesis of methylamines, outstanding selectivities for dimethylamine which exceed 70% by mole are obtained, and which can even reach 81.6% by mole, virtually without formation of trimethylamine and dimethyl ether, and with methanol conversions close to 100% by mole.

Accordingly, an object of the present invention is a process for the preparation of a modified ammonium mordenite characterized in that it comprises the steps of (1) drying an ammonium mordenite under conditions such that the mordenite is maintained in ammonium form and (2) treating the dried ammonium mordenite thus obtained with tetrachlorosilane in the gas phase at a temperature of between 300 and 600° C.

Another object of the present invention is a catalyst, more particularly, a catalyst for the preparation of methylamines from ammonia and methanol, comprising a modified ammonium mordenite obtained by the abovementioned process.

Finally, yet another object of the present invention is a process for the manufacture of methylamines, characterized in that a mixture of methanol and ammonia in the gas phase is passed at elevated temperature over a catalyst comprising a modified ammonium mordenite prepared by the abovementioned process.

The catalyst used according to the invention in the catalytic synthesis of methylamines from methanol and ammonia is prepared from an ammonium mordenite.

A mordenite is a crystalline aluminosilicate which either can be found directly in nature or is prepared by chemical synthesis. The overall composition of natural mordenites can be expressed generally by the formula $Na_8[(AlO_2)_8 (SiO_2)_{40}] \cdot 24H_2O$. Natural mordenites therefore have an Si/Al atomic ratio of 5:1. However, synthetic mordenites are also known in which the Si/Al ratio is higher than 5:1 (see pages 321–332 of the book by P. A. Jacobs and J. A. Martens, "Synthesis of High-Silica Aluminosilicate Zeolites", volume 33 of "Studies in Surface Science and Catalysis", Elsevier, 1987) or in which the sodium ions have been replaced with hydrogen, alkaline-earth or ammonium ions, or else with other alkaline ions.

The mordenite used as starting material for the preparation of the catalyst according to the present invention is an ammonium mordenite in which the Si/Al atomic ratio is between 5:1 and 20:1, preferably between 5:1 and 12:1. Its sodium content must be very low, preferably lower than 0.1% by weight relative to the weight of the mordenite. Ammonium mordenites are available commercially or can be prepared from a mordenite containing alkali or alkaline-earth metal ions as cations, by exchange of these ions with ammonium ions. This ion exchange may be performed by methods which are known per se, for example, by treatment with an aqueous solution of ammonium nitrate.

The ammonium mordenite which is suitable as catalyst according to the present invention is prepared by a process which essentially comprises a drying step followed by a silylation step.

With regard to the drying step, it must be performed under conditions such that the mordenite remains in the ammonium form. Indeed, we have found that above a temperature of 400° C., the ammonium mordenite is easily converted to a proton mordenite. This is why the drying step of the process according to the present invention is generally carried out at a temperature which is lower than 400° C., and preferably, at a temperature in the range of 230° C. to 350° C., in a stream of dry inert gas (nitrogen). The temperature and duration of drying must be sufficient to remove all the water adsorbed on the mordenite, but this temperature must not however be too high or the drying period too long, in order to avoid volatilizing chemically bound (chemisorbed) ammonia. The drying period is generally from 180 to 540 minutes, preferably from 360 to 480 minutes.

According to the present invention any process for drying the mordenite may be used. Thus, for example, the mordenite may be vacuum-dried, even at room temperature. Drying may therefore be performed at a pressure that is lower or higher than atmospheric pressure. Drying is preferably performed at a pressure that is lower than or equal to 3 bars.

During this drying step, the amount of water released may be checked, for example by condensing it at the reactor exit or by mass spectrometry analysis. Drying is stopped when water release has ended. Furthermore, analysis of the released gases, by bubbling into water and determining by titration the ammonia present in the aqueous solutions obtained, has shown that the quantity of ammonia which is released during the drying process is lower than 0.01% relative to the weight of mordenite used. The quantity of ammonia released during drying is therefore negligible with respect to the quantity of ammonia present in the initial mordenite.

At the end of this drying step, the dried product is allowed to cool under a stream of inert gas (nitrogen), in order to bring it back to room temperature.

Silylation of the dried ammonium mordenite is performed with tetrachlorosilane in the gas phase, by heating from room temperature, and gradually increasing the temperature at the rate of 1 to 5° C. per minute, preferably from 2.5 to 4° C. per minute, up to a temperature of 300 to 600° C., preferably from 450 to 550° C., and then maintaining this temperature for a period of 60 to 180 minutes, preferably from 120 to 160 minutes. Preferably, a gas mixture containing an inert gas and tetrachlorosilane is used, in which the partial pressure of tetrachlorosilane lies between 0.05 and 1.0 bar, in particular between 0.2 and 0.6 bar. During this silylation step a slight dealumination of the mordenite takes place: the Si/Al atomic ratio changes from an initial value of between 5:1 and 20:1 to a value of between 10:1 and 30:1.

According to the present invention, it is essential to use tetrachlorosilane as the silylating agent. Indeed, we have found that silylation by other silylating agents (dichlorodimethylsilane or polydimethylsiloxane) does not allow to obtain a catalyst that is selective for the formation of dimethylamine in the catalytic synthesis of methylamines from ammonia and methanol.

After cooling under an inert gas flow to room temperature, the treated mordenite is washed abundantly with distilled water in order to remove residual aluminium chlorides and aluminium salts. Washing is repeated several times until the pH of the supernatant solution becomes neutral. The modified ammonium mordenite thus obtained is then dried at 60° C. to constant weight.

The modified ammonium mordenites used as catalysts according to the present invention generally have an Si/Al atomic ratio of 10:1 to 30:1, preferably from 15:1 to 25:1.

The process for the preparation of the modified ammonium mordenite according to the invention is simpler and less expensive than the processes of the state of the art. In fact, contrary to the process for the preparation of a modified mordenite disclosed in U.S. Pat. Nos. 5,137,854 and 5,210,308, which comprises four essential steps, including two calcination steps, the process for the preparation of the modified ammonium mordenite according to the present invention takes place in two steps (drying and silylation), without involving a calcination step. In addition, the process according to the present invention is easier to carry out than the process according to European Patent Application 593,086, in which scrupulous care must be taken to adjust the water content in the mordenite at a predetermined value before the silylation step, and in which several calcinations are also performed.

It follows that the process for the preparation of the modified ammonium mordenite according to the present invention is easily and economically applicable on an industrial scale, as opposed to the processes of the state of the art.

In the process for the synthesis of methylamines according to the present invention, the methanol and ammonia used as starting materials may be pure or, for obvious economic reasons, of technical grade.

The raw materials are used in the process according to the invention in quantities such that the nitrogen/carbon (N/C) atomic ratio is from 0.5:1 to 5:1, preferably from 0.8:1 to 2:1.

When the N/C atomic ratio increases, the selectivity for the production of dimethylamine tends to decrease, whereas when the N/C atomic ratio decreases, the production of trimethylamine increases. This is why it is not recommended to work with an N/C atomic ratio outside the range of 0.5:1 to 5:1.

The methanol feed rate is advantageously between 0.1 and 2 kg/h/kg of catalyst.

The operating conditions used in the process of the invention are those generally used for the manufacture of methylamines by gas phase catalytic reaction of ammonia with methanol. The process is generally performed in a temperature range of between 220 and 350° C., preferably between 280 and 320° C., at a pressure ranging from atmospheric pressure to approximately 100 bars, preferably ranging from approximately 1 to 50 bars.

No restrictions are imposed regarding the nature of the apparatus used to perform the process of the invention. The process may be conducted continuously or noncontinuously. The catalyst bed may be a stationary or fluidized bed.

At the reactor exit, the gas mixture is separated into its various constituents by methods which are known per se, for example by fractional distillation. After separation of the various constituents of the reactor effluent, ammonia, monomethylamine and/or dimethylamine may, if desired, be partially or completely recycled.

In the process according to the invention, which uses a modified ammonium mordenite prepared as described above as catalyst, very high selectivities for the production of dimethylamine are very easily obtained, which may reach from 72 to 82% by mole, with methanol conversions close to 100% by mole. In addition, practically no trimethylamine is formed, nor are by-products such as dimethyl ether.

Furthermore, the same good results are obtained when the gas mixture of methanol and ammonia contains monomethylamine and/or dimethylamine and/or trimethylamine. The methylamines formed can therefore be recycled with the ammonia in the gas mixture which is fed to the reactor without affecting the selective production of dimethylamine. This constitutes a considerable industrial advantage. Finally, as shown later in the examples, the catalyst retains its activity and its selectivity for a long period.

The examples which follow illustrate the present invention without limiting it. In these examples the Si/Al atomic ratios mentioned were determined by $^{29}$Al Magic Angle Spinning Nuclear Magnetic Resonance (abbreviated MAS NMR), using, as reference, a mordenite containing exclusively aluminium atoms in tetrahedral sites, the aluminium content of which was determined by the coupled inductive plasma technique as described by D. R. Corbin et al. in Anal.Chem. 59 (1987), 2722–2728.

EXAMPLE 1

Preparation of the Catalyst According to the Invention

In this example the mordenite used is PQ Zeolite CBV 20A (The PQ Corporation, Valley Forge, United States), which is a synthetic ammonium mordenite, with a low Na content (0.01% by weight relative to the weight of mordenite). This mordenite has an Si/Al atomic ratio of 10:1 and a content of nitrogen in the form of ammonia of 1.95% by weight. The ammonia content was determined by displacement of the $NH_4^+$ ions of the mordenite with a concentrated aqueous solution of sodium hydroxide, followed by steam distillation of the ammonia formed, condensation of the steam and determination of the ammonia in the aqueous solution thus obtained.

(1) Drying.

Approximately 25 g of mordenite are pelleted and thieved to give 10 g of pellets which have a particle size of between 250 and 500 μm. The fraction of mordenite having this particle size is introduced into a quartz tube of 25 mm in diameter, equipped with a thermowell. The portion of the tube used is heated externally by an electrical coil placed in such a way that it ensures a uniform temperature in the catalyst bed. The mordenite is heated up to 300° C. at atmospheric pressure at a rate of 2.5° C./min in a stream of nitrogen at a flow rate of 40 ml/min and the mordenite is kept at this temperature of 300° C. for 5 hours. It is then allowed to cool to room temperature under a stream of dry nitrogen. Analysis shows that the amount of ammonia released during this drying step is negligible with respect to the weight of mordenite used.

(2) Treatment with Tetrachlorosilane.

A stream of nitrogen is passed through a bubbler containing tetrachlorosilane, maintained at a temperature ensuring a partial tetrachlorosilane pressure of approximately 0.24 bar. The gas mixture of nitrogen and tetrachlorosilane is then brought onto the catalyst bed (dried mordenite) at a flow rate of 40 ml/min, the catalyst bed being gradually heated to 550° C. at a rate of 3.5° C./min. The mordenite is kept at 550° C. for 2 additional hours under the gas stream and is then allowed to cool to room temperature under nitrogen.

The mordenite thus treated is suspended in 2 litres of distilled water, the water is decanted off and this operation is repeated until the pH of the supernatant solution is neutral. The mordenite thus obtained is then dried at 60° C. to constant weight. The modified ammonium mordenite thus obtained has an Si/Al atomic ratio of 25:1. Its content of nitrogen in the form of ammonia is 0.7% by weight. The ammonia content is determined by displacement of the $NH_4^+$ ions with a concentrated aqueous solution of sodium hydroxide, followed by steam distillation of the ammonia formed, condensation of the steam and determination of the ammonia in the aqueous solution thus obtained.

In the case of a mordenite which has an Si/Al atomic ratio of 25:1, this nitrogen content means that the mordenite obtained after silylation is still in the ammonium form. In fact, the theoretical general formula of such a mordenite should be $(NH_4)_{1.85}[(AlO_2)_{1.85}(SiO_2)_{46.15}]\cdot 24H_2O$, and its theoretical molecular weight would therefore be 3550. The theoretical nitrogen content expressed in per cent by weight relative to the total weight of mordenite is therefore $[(14\times 1.85)/3550]\times 100 = 0.73\%$ by weight.

Since the experimental nitrogen content is 0.7% by weight relative to the weight of mordenite, it is clear that the mordenite is still in the ammonium form after the silylation treatment according to the invention is performed.

EXAMPLE 2 (comparative)

Preparation of Catalysts Based on Various Zeolites

In this example the process used is the same as in Example 1, except it is applied to various commercial or synthetic zeolites. The aim of the preparation of these catalysts based on various zeolites is to compare their performance in the synthesis of methylamines from ammonia and methanol with the performance of the modified ammonium mordenite prepared according to the process of the invention (see Example 4 below).

2.1. Silylation of zeolite Beta $H^+$.

Preparation is performed exactly as in the preparation of the catalyst of Example 1 but the starting mordenite is replaced with zeolite Beta $H^+$ CP 811-25 (PQ Zeolites B.V., Leiden, Netherlands), which is a synthetic proton zeolite with an Si/Al atomic ratio of 13:1. The modified zeolite Beta $H^+$ thus obtained has an Si/Al ratio of 150:1.

2.2. Silylation of zeolite Beta $Na^+$.

a) Zeolite Beta $H^+$ CP 811-25 used in Example 2.1 above is converted to a Beta zeolite in sodium form by stirring in an aqueous solution of $NH_3$ at room temperature, followed by stirring in an aqueous solution of sodium chloride at reflux temperature for 4 hours. It is then washed with distilled water until no more chloride ions are detected, then dried at 60° C.

b) The Beta zeolite in sodium form prepared in 2.2.a) is next dried and treated exactly as in Example 1, to give a modified zeolite Beta $Na^+$ with an Si/Al atomic ratio of 40:1.

2.3. Silylation of a sodium mordenite.

a) The ammonium mordenite PQ Zeolite CBV 20A used in Example 1 is converted into its sodium form by stirring in an aqueous solution of sodium chloride at reflux temperature for 4 hours. It is then washed with distilled water until no more chloride ions are detected and then dried at 60° C.

A sodium mordenite is obtained having an Si/Al atomic ratio of 10:1.

b) The sodium mordenite prepared in 2.3.a) is next dried and treated exactly as described in Example 1, to give a modified sodium mordenite having an Si/Al atomic ratio of 17:1.

EXAMPLE 3 (comparative)

Preparation of the Catalyst Described in U.S. Pat. No. 5,137,854

By way of comparison, a modified proton mordenite was also prepared according to the process described in U.S. Pat. No. 5,137,854.

3.1. The ammonium mordenite PQ Zeolite CBV 20A used in Example 1 is converted into its sodium form by stirring in an aqueous solution of sodium chloride at reflux temperature for 4 hours. It is then washed with distilled water until no more chloride ions are detected and then dried at 60° C. A sodium mordenite is obtained which has an Si/Al atomic ratio of 10:1.

3.2. Next, the method of preparation of the catalyst described in the example of U.S. Pat. No. 5,137,854 (column 6, line 50 to column 7, line 34) is reproduced exactly using the sodium mordenite prepared in 3.1 above. In this process, the sodium mordenite is heated in a stream of nitrogen at 700° C. for 30 minutes and is then subjected at this temperature to a gas stream of tetrachlorosilane and nitrogen for approximately 3 hours; the mordenite thus treated is washed with distilled water until no more chloride ions are detected, it is subjected to calcination at 450° C., the sodium ions of the mordenite are exchanged with ammonium ions by treatment with a solution of $NH_4NO_3$, and the ammonium mordenite thus obtained is finally subjected to another calcination for 2 hours at 450° C. A modified proton mordenite is obtained which has an Si/Al atomic ratio of 10:1.

EXAMPLE 4

Synthesis of Methylamines

In this example the catalytic performances of a modified ammonium mordenite prepared according to the process of the invention (cf. Example 1) are compared with those of various other zeolites treated or untreated with tetrachlorosilane.

4.1 Apparatus and operating conditions.

The reactor used is a Pyrex glass tube with a height of 50 cm and an internal diameter of approximately 22 mm. A thermowell in which a thermocouple may slide runs through the centre of this tube, in order to allow close monitoring of the catalyst temperature. This tube is placed in a fluidized sand bath heated externally by an electrical resistance so as to ensure a uniform temperature distribution. In the tube, the layer of the catalyst subjected to trial is preceded by a layer of inert material (α-alumina) which is used to preheat the gaseous reactants before they pass over the catalyst bed. 7 grams of catalyst in the form of ground pellets having a particle size of between 300 and 400 μm are used for the trials; the catalyst is additionally diluted with an inert material.

The mixture of ammonia and methanol in the gas phase is fed to the reactor from the top downwards. The reaction is performed at a temperature of 300° C., at atmospheric pressure and with a methanol feed rate of 0.3 kg/h/kg of catalyst. The ammonia feed rate is such that an N/C atomic ratio of 2:1 is produced. Experience shows that these trials, performed at atmospheric pressure with a gas mixture of methanol, ammonia and possibly recycled methylamines, constitute a good method of comparison of the catalysts, as well as a reliable basis for extrapolation to higher pressure conditions.

At the exit of the reactor, a known flow rate of nitrogen dilutes the exiting gas products and prevents their condensation. Analysis of the composition of the gas mixture is performed by gas phase chromatography.

4.2. Comparison of the catalyst performances.

The results obtained for each catalyst tested in the synthesis of methylamines under the conditions described at Example 4.1. are given in Table I below.

In this table the terms used have the following meanings:
zeolite Beta H$^+$: zeolite Beta H$^+$ CP 811-25 sold by PQ Zeolites B.V., Leiden, Netherlands;
zeolite Beta H$^+$.SiCl$_4$: the silylated zeolite prepared in Example 2.1;
zeolite Beta Na$^+$.SiCl$_4$: the silylated zeolite prepared in Example 2.2.;
calcined zeolite ZSM-12 NH$_4^+$: sodium zeolite, obtained according to the method described at page 13 (Example 6a) of the book by P. A. Jacobs and J. A. Martens "Synthesis of High-silica Aluminosilicate Zeolites", volume 33 of "Studies in Surface Science and Catalysis", Elsevier, 1987, which is then exchanged with an aqueous solution of NH$_3$ at room temperature and calcined at 500° C. for 4 hours in the presence of air.
calcined mordenite NH$_4^+$: mordenite PQ zeolite CBV 20A (The PQ Corporation, Valley Forge, United States), calcined at 500° C. for 4 hours in the presence of air.
mordenite 100 H$^+$: commercial highly dealuminized proton mordenite, which has an Si/Al ratio of 100:1 (sold by Zeocat 44550, Montoir de Bretagne, France);
mordenite Na$^+$.SiCl$_4$: the silylated mordenite prepared in Example 2.3.;
mordenite SiCl$_4$.H$^+$: the silylated mordenite prepared in Example 3 according to the process disclosed in U.S. Pat. No. 5,137,854.
mordenite NH$_4^+$.SiCl$_4$: the modified ammonium mordenite prepared in Example 1 (according to the invention);

Si/Al: the Si/Al atomic ratio of the catalyst used;

$C_{MeOH}$: the methanol conversion (in % by mole) calculated by the formula $$C_{MeOH} = 100 - \frac{\text{moles of unconverted methanol}}{\text{moles of methanol fed}} \times 100;$$

$S_{DME}$: the selectivity for dimethyl ether (in % by mole), calculated by the formula $$S_{DME} = \frac{2 \times \text{moles of DME}}{2 \times \text{moles of DME} + 1 \times \text{moles of MMA} + 2 \times \text{moles of DMA} + 3 \times \text{moles of TMA}} \times 100;$$

$S_{MMA}$: the selectivity for monomethylamine (in % by mole), calculated by the formula $$S_{MMA} = \frac{1 \times \text{moles of MMA}}{2 \times \text{moles of DME} + 1 \times \text{moles of MMA} + 2 \times \text{moles of DMA} + 3 \times \text{moles of TMA}} \times 100;$$

$S_{DMA}$: the selectivity for dimethylamine (in % by mole), calculated by the formula $$S_{DMA} = \frac{2 \times \text{moles of DMA}}{2 \times \text{moles of DME} + 1 \times \text{moles of MMA} + 2 \times \text{moles of DMA} + 3 \times \text{moles of TMA}} \times 100;$$

$S_{TMA}$: the selectivity for trimethylamine (in % by mole), calculated by the formula $$S_{TMA} = \frac{3 \times \text{moles of TMA}}{2 \times \text{moles of DME} + 1 \times \text{moles of MMA} + 2 \times \text{moles of DMA} + 3 \times \text{moles of TMA}} \times 100;$$

In these formulae,
MeOH=methanol
DME=dimethyl ether
MMA=monomethylamine
DMA=dimethylamine
TMA=trimethylamine

TABLE I

| Catalyst | Si/Al | $C_{MeOH}$ (% by mole) | $S_{DME}$ (% by mole) | $S_{MMA}$ (% by mole) | $S_{DMA}$ (% by mole) | $S_{TMA}$ (% by mole) |
|---|---|---|---|---|---|---|
| zeolite Beta H$^+$ | 13:1 | >99 | 0.5 | 32 | 24 | 44 |
| zeolite Beta H$^+$ · SiCl$_4$ | 150:1 | 81 | | 12* | 12 | 76 |
| zeolite Beta Na$^+$ · SiCl$_4$ | 40:1 | 96 | | 17* | 22 | 61 |
| calcined zeolite ZSM-12 NH$_4^+$ | 45:1 | 86 | | 12* | 23 | 65 |
| calcined mordenite NH$_4^+$ | 8:1 | >98 | 0.5 | 15 | 25 | 60 |
| mordenite 100 H$^+$ | 100:1 | 93 | | 21* | 21 | 58 |
| mordenite | 17.2:1 | >98 | 2 | 38 | 38 | 22 |

TABLE I-continued

| Catalyst | Si/Al | $C_{MeOH}$ (% by mole) | $S_{DME}$ (% by mole) | $S_{MMA}$ (% by mole) | $S_{DMA}$ (% by mole) | $S_{TMA}$ (% by mole) |
|---|---|---|---|---|---|---|
| $Na^+ \cdot SiCl_4$ mordenite | 10:1 | 97 | 2 | 20 | 51 | 27 |
| $SiCl_4 \cdot SiCl_4$ mordenite | 25:1 | 97 | 0.4 | 27.2 | 72.1 | 0.3 |
| $NH_4^+ \cdot SiCl_4$ (accoring to the invention) | | | | | | |

*$S_{DME} + S_{MMA}$

Table I clearly shows that zeolites Beta and ZSM-12 promote the production of trimethylamine to the detriment of the production of dimethylamine. In fact, the methylamine compositions obtained with these zeolites are very close to the values that can theoretically be reached when thermodynamic equilibrium between the three methylamines is achieved. These zeolites are therefore not very selective for the production of dimethylamine.

Furthermore, Table I shows that mordenites generally exhibit very good activity with high methanol conversions. The unsilylated proton mordenites (calcined mordenite $NH_4^+$ and mordenite 100 $H^+$) also promote the formation of trimethylamine rather than dimethylamine. The silylated sodium mordenite (mordenite $Na^+.SiCl_4$) is more selective for the production of dimethylamine (38% by mole). However, the selectivity for trimethylamine remains high (22% by mole).

The sodium mordenite treated with $SiCl_4$ and converted into a proton mordenite, prepared according to the process disclosed in U.S. Pat. Nos. 5,137,854 and 5,210,308, is highly selective for the production of dimethylamine (51% by mole). However, the production of trimethylamine remains high, since the selectivity for trimethylamine is of 27% by mole.

Table I clearly shows the superiority of the mordenite-based catalyst prepared according to the process of the invention when compared with the catalysts based on other zeolites, whether treated or not with $SiCl_4$. In fact, the ammonium mordenite treated according to the invention with tetrachlorosilane in the gas phase at elevated temperature constitutes the most selective catalyst for the production of dimethylamine, with a selectivity for DMA of 72.1% by mole; moreover, with this catalyst, the production of trimethylamine and of dimethyl ether is extremely low (0.7% by mole for the combined total of these two products) and the methanol conversion is almost complete (97% by mole).

EXAMPLE 5

Influence of the N/C Atomic Ratio

In this example, the conditions for the synthesis of methylamines are varied in order to determine the optimum use conditions of the catalyst according to the invention.

The same operating conditions as in Example 4 are used, using the modified ammonium mordenite prepared in Example 1 as catalyst, at 300° C., but varying the N/C atomic ratio and the methanol feed rate (number of kilograms of methanol per hour per kilogram of catalyst).

The results obtained are given in Table II, in which $C_{MeOH}$, $S_{DME}$, $S_{MMA}$, $S_{DMA}$ and $S_{TMA}$ have the same meaning as in Example 4.

TABLE II

| Atomic ratio N/C | MeOH flow rate (kg/h/kg of catalyst) | $C_{MeOH}$ (% by mole) | $S_{DME}$ (% by mole) | $S_{MMA}$ (% by mole) | $S_{DMA}$ (% by mole) | $S_{TMA}$ (% by mole) |
|---|---|---|---|---|---|---|
| 1.3:1 | 0.2 | >99 | 0.8 | 16.2 | 77.0 | 6.0 |
| 1.3:1 | 0.3 | >99 | 0.6 | 17.7 | 81.6 | 0.1 |
| 1.6:1 | 0.2 | >99 | 0.7 | 21.1 | 76.2 | 2.0 |
| 1.6:1 | 0.3 | >99 | 0.5 | 21.3 | 77.7 | 0.4 |
| 2.0:1 | 0.2 | 99 | 0.4 | 25.5 | 72.5 | 1.6 |
| 2.0:1 | 0.3 | 97 | 0.4 | 27.2 | 72.1 | 0.3 |

Table II shows that at 300° C. and with a methanol feed rate of 0.3 kg/h/kg of catalyst, the production of trimethylamine is practically nil and that of dimethyl ether is very low, close to 0.5 %, regardless of the N/C atomic ratio in the feed gases. The selectivity for dimethylamine can reach 81.6% by mole in the case of an N/C atomic ratio of 1.3. It also shows that the selectivity for dimethylamine decreases when the N/C atomic ratio increases.

EXAMPLE 6

Influence of the Reaction Temperature

The reaction is carried out under the same conditions as in Example 4, using the modified ammonium mordenite prepared in Example 1 as catalyst, except that the reaction temperature is lowered. The results obtained are given in Table III, in which $C_{MeOH}$, $S_{DME}$, $S_{MMA}$, $S_{DMA}$ and $S_{TMA}$ have the same meaning as in Example 4.

TABLE III

| Temperature (° C.) | Atomic ratio N/C | MeOH flow rate (kg/h/kg of catalyst) | $C_{MeOH}$ (mol %) | $S_{DME}$ (mol %) | $S_{MMA}$ (mol %) | $S_{DMA}$ (mol %) | $S_{TMA}$ (mol %) |
|---|---|---|---|---|---|---|---|
| 280 | 1.6:1 | 0.1 | >98 | 0.5 | 20 | 76 | 3.5 |
| 260 | 1.6:1 | 0.1 | 64 | 2 | 46 | 52 | <0.1 |

Table III shows that at lower temperatures, in other words, at incomplete methanol conversion, the performances of the catalyst according to the invention are still very good; the formation of trimethylamine and of dimethyl ether remains very low.

EXAMPLE 7

Stability of the Catalyst

The synthesis of methylamines is performed as described in Example 4, using the modified ammonium mordenite prepared in Example 1 as catalyst. This catalyst is maintained for 70 days at 300° C., at atmospheric pressure, with an N/C atomic ratio in the feed gases of 2:1 and a methanol feed rate of 0.2 kg/h/kg of catalyst. During this period the catalyst retains its activity with a methanol conversion higher than 99% by mole and a selectivity for dimethylamine which remains constant at 73% by mole.

EXAMPLE 8

Conversion of Monomethylamine

In this example, the performance of the catalyst according to the invention is studied in the synthesis of methylamines from a gas mixture of ammonia and methanol containing monomethylamine.

The reaction is carried out under the same conditions as in Example 4, using the modified ammonium mordenite prepared in Example 1 as catalyst, at a reaction temperature of 300° C., except a gas mixture of ammonia, methanol and monomethylamine is fed to the reactor in quantities such that the N/C atomic ratio is 2:1, with a methanol flow rate of 0.1 kg/h/kg of catalyst and a monomethylamine flow rate of 0.2 kg/h/kg of catalyst. Under these conditions the methanol conversion is higher than 99% by mole and the selectivity for dimethylamine is of 73% by mole. From this, we conclude that the monomethylamine formed can be easily recycled into the gas mixture fed to the reactor and can itself be converted into dimethylamine.

EXAMPLE 9

In this example, the performance of the catalyst according to the invention is studied in the synthesis of methylamines from a gas mixture of ammonia and methanol containing trimethylamine.

The reaction is carried out under the same conditions as in Example 4, using the modified ammonium mordenite prepared in Example 1 as catalyst, at a reaction temperature of 300° C., except that a gas mixture of ammonia, methanol and trimethylamine is fed to the reactor in quantities such that the N/C atomic ratio is 2:1, with a methanol flow rate of 0.1 kg/h/kg of catalyst and a trimethylamine flow rate of 0.067 kg/h/kg of catalyst. Under these conditions, the methanol conversion is of 100% by mole, with a selectivity for dimethylamine of 70% by mole. In addition, the quantity of trimethylamine found at the reactor exit is the same as that at the reactor entry.

What is claimed is:

1. A process for the preparation of a modified ammonium mordenite, comprising the steps of:
   (1) drying an ammonium mordenite at a temperature lower than 400° C. such that the mordenite is maintained in ammonium form to obtain a dried ammonium mordenite, and
   (2) treating the dried ammonium mordenite with tetrachlorosilane in a gaseous phase at a temperature of between 300 and 600° C.

2. The process according to claim 1, wherein the drying step is performed at a temperature in the range of 230 to 350° C., for a period of 180 to 540 minutes.

3. The process according to claim 1, wherein the drying step is performed at a pressure that is lower than or equal to 3 bars.

4. The process according to claim 1, wherein the tetrachlorosilane treatment step is performed at atmospheric pressure at a temperature of 450 to 550° C. for a period of 60 to 180 minutes.

5. The process according to claim 1, wherein the modified ammonium mordenite has an Si/Al atomic ratio of 10:1 to 30:1.

6. A catalyst comprising a modified ammonium mordenite prepared by the process according to claim 1.

7. A catalyst for the preparation of methylamines from ammonia and methanol, comprising a modified ammonium mordenite prepared by the process according to claim 1.

8. A process for the manufacture of methylamines, which comprises the step of passing a mixture of methanol and ammonia in a gaseous phase at an elevated temperature over a catalyst comprising a modified ammonium mordenite prepared by the process according to claim 1.

9. The process according to claim 8, wherein the methanol and ammonia mixture has a nitrogen/carbon atomic ratio of from 0.5:1 to 5:1.

10. The process according to claim 8, wherein the methanol feed rate is between 0.1 and 2 kg/h/kg of catalyst.

11. The process according to claim 8, wherein the reaction is performed a temperature of between 220° C. and 350° C.

12. The process according to claim 8, wherein the reaction is performed at a pressure between atmospheric pressure and 100 bars.

13. The process according to claim 8, wherein the mixture of methanol and ammonia contains monomethylamine and/or dimethylamitie and/or trimethylamine.

14. A process for the preparation of a modified ammonium mordenite, comprising the step of treating a dried ammonium mordenite with tetrachlorosilane in gaseous phase at a temperature of between 300 and 600° C.

15. The process according to claim 14, wherein the dried ammonium mordenite is prepared by drying an ammonium mordenite at a temperature lower than 400° C. such that the mordenite is maintained in ammonium form.

16. A catalyst comprising a modified ammonium mordenite prepared by the process according to claim 14.

17. A process for the manufacture of methylamines, which comprises the step of passing a mixture of methanol and ammonia in a gaseous phase at an elevated temperature over a catalyst comprising a modified ammonium mordenite prepared by the process according to claim 14.

* * * * *